(12) United States Patent
Richardson et al.

(10) Patent No.: US 7,593,509 B2
(45) Date of Patent: Sep. 22, 2009

(54) ANALYTICAL X-RAY TUBE FOR CLOSE COUPLED SAMPLE ANALYSIS

(75) Inventors: John Richardson, Layton, UT (US); Robert Treseder, Lynchburg, VA (US)

(73) Assignee: Varian Medical Systems, Inc., Palo Alto, CA (US)

( * ) Notice: Subject to any disclaimer, the term of this patent is extended or adjusted under 35 U.S.C. 154(b) by 19 days.

(21) Appl. No.: 11/863,124

(22) Filed: Sep. 27, 2007

(65) Prior Publication Data

US 2009/0086898 A1    Apr. 2, 2009

(51) Int. Cl.
*H01J 35/08* (2006.01)
*H01J 35/14* (2006.01)

(52) U.S. Cl. ................... 378/137; 378/121; 378/143
(58) Field of Classification Search .......... 378/119–144
See application file for complete search history.

(56) References Cited

U.S. PATENT DOCUMENTS

| | | | | |
|---|---|---|---|---|
| 2,958,799 | A * | 11/1960 | Rimsky et al. | ............... 378/124 |
| 3,072,789 | A | 1/1963 | Ladell et al. | |
| 3,102,952 | A | 9/1963 | Hendee et al. | |
| 3,270,200 | A | 8/1966 | Rhodes | |
| 3,508,059 | A * | 4/1970 | Vanderpool | ................. 378/102 |
| 3,925,660 | A | 12/1975 | Albert | |
| 4,017,757 | A * | 4/1977 | DeCou, Jr. | ................... 378/124 |
| 4,131,794 | A | 12/1978 | Bruninx | |
| 4,260,885 | A | 4/1981 | Albert | |
| 4,461,017 | A | 7/1984 | Koga et al. | |
| 4,688,241 | A * | 8/1987 | Peugeot | ...................... 378/137 |
| 4,870,671 | A * | 9/1989 | Hershyn | ...................... 378/124 |
| 5,257,302 | A | 10/1993 | Narukawa | |
| 5,398,274 | A | 3/1995 | Komatani et al. | |
| 5,406,609 | A | 4/1995 | Arai et al. | |
| 5,428,656 | A | 6/1995 | Kira et al. | |
| 5,732,120 | A | 3/1998 | Shoji et al. | |
| 7,140,771 | B2 * | 11/2006 | Leek | .......................... 378/203 |

* cited by examiner

*Primary Examiner*—Edward J Glick
*Assistant Examiner*—Thomas R Artman
(74) *Attorney, Agent, or Firm*—Workman Nydegger

(57) ABSTRACT

In one example, an x-ray device is provided that includes an enclosure having an x-ray transmissive window. A cathode assembly that includes an electron source capable of emitting electrons is disposed within the enclosure. An anode is also disposed in the enclosure between the cathode assembly and the window. The anode includes a body portion and a target surface that is positioned on the body portion so as to face away from the electron source of the cathode assembly. The anode further includes a drift tunnel that defines a path through which electrons pass from the electron source to the target surface. Finally, this example includes a voltage source electrically connected so as to provide a potential field that causes some of the electrons to impact the target surface and produce x-rays for emission through the window.

29 Claims, 3 Drawing Sheets

ANALYTICAL X-RAY TUBE FOR CLOSE COUPLED SAMPLE ANALYSIS

BACKGROUND OF THE INVENTION

1. The Field of the Invention

The present invention relates generally to x-ray tube devices. In particular, embodiments of the present invention relate to analytical x-ray tubes employing a cathode assembly—target surface arrangement which contributes to reduced heat levels in various portions of the x-ray tube, and which allows the x-ray tube to be placed relatively closer to the sample to be analyzed, thereby improving the quality of the analysis that can be performed with the x-ray tube.

2. Prior State of the Art

X-ray producing devices are extremely valuable tools that are used in a wide variety of applications, both industrial and medical. Such equipment is commonly used in applications such as diagnostic and therapeutic radiology, semiconductor manufacture and fabrication, materials testing, and sample analysis. While used in a number of different applications, the basic operation of x-ray tubes is similar. In general, x-rays, or x-ray radiation, are produced when electrons are produced, accelerated, and then impinged upon a material of a particular composition.

Regardless of the application in which they are employed, these devices typically include a number of common elements including a cathode, or electron source, and an anode situated within an evacuated enclosure. The anode includes a target surface which receives electrons emitted by the cathode. In operation, an electric current applied to a filament portion of the cathode causes electrons to be emitted from the filament by thermionic emission. The electrons thus emitted are accelerated towards a target surface of the anode under the influence of an electric potential established between the cathode and the anode. The interaction of these high energy electrons on the target surface causes x-rays to be emitted from the target surface.

The specific frequency of the x-rays produced depends in large part on the type of material used to form the anode target surface. Anode target surface materials with high atomic numbers ("Z" numbers), such as tungsten, are typically employed. The x-rays ultimately exit the x-ray tube through a window in the tube, and interact in or on various material samples or patients. As is well known, the x-rays can be used for sample analysis procedures, therapeutic treatment, or in medical diagnostic applications.

As discussed above, a portion of the electrons that impact the anode target surface convert some portion of their kinetic energy to x-rays. However, most of the kinetic energy does not produce usable x-rays, but is released in the form of heat. This heat, which can reach extremely high temperatures, is transferred throughout the anode and other x-ray tube structures, such as the window.

Some of the electrons simply rebound from the target surface and strike other "non target" surfaces within the x-ray tube. These are often referred to as "backscatter" or secondary electrons. These backscatter electrons retain a significant amount of kinetic energy after rebounding, and thus when they impact non-target surfaces such as the window, additional heat is generated.

The heat generated at the target surface as a result of normal x-ray tube operations, as well as the heat generated as a consequence of backscatter electron impacts, must be reliably and continuously removed. If left unchecked, such heat can compromise the performance of the x-ray tube, or damage it, and may ultimately shorten its operational life. As discussed below, the heat imparted to the window area is especially problematic in the context of analytical x-ray tubes (AXT).

In general, AXTs refer to a type of x-ray device that is typically used to produce a stream of x-rays that can be employed to facilitate, among other things, analysis and evaluation of material samples. Examples of analytical, evaluative, and control processes that can be performed or facilitated by AXTs include material composition analysis, fracture detection and evaluation, industrial material content control, thickness of material control and the like. AXTs possess a variety of useful characteristics that make them well suited for such applications. For example, AXTs are relatively compact and portable. Furthermore, AXTs produce results relatively quickly. Finally, the x-rays emitted by the AXTs are non-destructive to the sample being analyzed. This feature is particularly useful in that it facilitates, among other things, analysis/evaluation of materials in situ.

The operation of a typical AXT is relatively straightforward. Typically, a sample of material is bombarded with x-rays from the AXT. One or more detectors or other sensors placed near the sample are then used to capture, categorize, or otherwise sense the response of the sample material.

As is well known, different materials generally respond in different ways to the presence of x-rays. That is, as a consequence of variables such as chemical composition and structure, each material exhibits a characteristic response when struck by x-rays. Thus, when the beam of x-rays generated by the AXT is directed toward a sample of interest, the sample responds in a characteristic fashion that distinguishes it from other materials. Based upon the response exhibited by the sample, the user of the AXT is able to draw conclusions regarding the nature of the sample being analyzed.

One example of an analytical technique where AXTs are commonly employed is commonly known as x-ray fluorescence spectroscopy ("XRF"). In XRF applications, the sample is bombarded with a beam of x-rays from the AXT. The material responds by emitting characteristic x-rays which are received or sensed by the detector so as to facilitate evaluation of the sample.

It is generally the case that the quality of the results obtainable with an AXT improves as the distance between the target surface and the material sample decreases. This is at least partly due to the fact that a relatively shorter distance between the target surface and the sample translates to a relative increase in the number of x-rays striking the sample, and accordingly, an improved response from the sample. This consideration, among others, has lead to the development of AXTs having relatively compact geometrical arrangements.

In particular, the typical AXT employs a cathode disposed in close proximity to the target surface so as to maximize the electric field at the cathode, and hence the number of electrons striking the target surface, and thus, the x-ray flux produced by the device. As previously noted, the quality of sample analysis increases as a function of the proximity of the target to the sample. Thus, in an effort to improve the quality of analysis performed by AXTs, many design efforts have focused on attempting to compress the distance between the window and the target surface, as well as the distance between the sample and AXT window.

As noted earlier however, the cathode in a typical AXT is located near the target surface so as to maximize x-ray production by the device. Thus, as the target surface is moved closer to the window, the distance between the cathode and the window necessarily decreases as well. While such arrangements may enhance some aspects of the performance of the AXT, they have proven problematic for a variety of reasons.

One problem with such arrangements concerns electron bombardment of the window and surrounding structures. In particular, because the window is so close to the cathode, a large number of electrons emitted by the cathode inevitably strike the window, thereby imparting a significant amount of heat to the window and surrounding structures.

This problem has not gone unnoticed, and various attempts have been made to devise systems and structures to counteract the high heat levels typically present in the window area of known AXTs. However, while such systems and structures arguably provide a level of cooling in the window area, they also add to the overall complexity and bulk of the AXT. Additionally, the addition of window cooling devices and systems increases the overall cost of the AXT.

Another problem stemming from the proximity of the cathode to the window concerns the effects of the cathode filament material, typically tungsten, on the inner window surface. In particular, the high filament temperature required for electron emission causes a thin film of tungsten from the filament to be deposited on the inside window surface. The film of tungsten thus deposited blocks some x-rays from passing through the window and accordingly, a reduction of x-ray output through the window to the sample is realized. As is well known, the quality of analysis achievable with the AXT is at least partially a function of the x-ray output of the AXT. Accordingly, the reduction in x-ray output that stems from the formation of the tungsten film on the inner window surface acts to materially compromise the performance of the AXT.

Another problem posed by the tungsten film deposited on the inner window surface concerns the integrity of the characteristic response emitted by the sample undergoing analysis. In particular, because some of the x-rays produced by the AXT strike the tungsten film prior to impinging upon the sample, stray emissions are generated that contaminate and compromise the characteristic response emitted by the sample.

Finally, while efforts have been made to produce AXTs of relatively compact configuration, certain inherent features of components used in the x-ray generation process practically limit the extent to which such compactness may be achieved. In particular, the high voltages typically employed in AXT and other x-ray devices necessitate the maintenance of predetermined physical clearances between various structures such as the window, target and cathode. For example, structures that are at sufficiently different potentials, relative to each other, will cause arcing if they are placed too close together. At best, such arcing compromises the performance of the device, and may in some cases, cause a complete failure of the device. Thus, the high operational voltages serve to impose practical limits on the extent to which such structures can be moved more closely together.

Because of such limits, the overall compactness of the AXT is necessarily limited as well. As discussed above, the quality of analysis achievable with a particular AXT is at least partially a function of the distance between the target surface and the sample to be analyzed. Thus, the quality of the analysis performed is inherently limited by geometric arrangements which are, in turn, at least partially dictated by the high voltages typically employed by these devices.

One specific example of such geometric limitations concerns the nose portion of the x-ray tube evacuated housing where the window is located. Typically, the nose portion of AXTs is relatively wide so as to accommodate the spacing requirements imposed by the high voltages present in the device. In particular, the relative width of the nose permits the various components of the AXT to be positioned so as to avoid problems such as arcing. However, wide nose portions in many cases limit the usefulness of AXTs in confined spaces or close quarters by preventing close coupling of the target with the sample to be analyzed, and by preventing the x-ray detectors from being positioned in their optimum location.

In view of the foregoing problems and shortcomings with existing x-ray devices, and AXTs in particular, it would be an advancement in the art to provide an AXT employing a cathode and anode arrangement that would substantially minimize heating of the window and surrounding structures and that would substantially foreclose formation of filament deposits on the window, all without compromising the performance of the AXT. Additionally, the AXT should employ a relatively compact geometry so as to facilitate close coupling of the AXT with the sample to be analyzed.

SUMMARY OF THE INVENTION

The present invention has been developed in response to the current state of the art, and in particular, in response to these and other problems and needs that have not been fully or adequately solved by currently available analytical x-ray tubes and devices. In general, embodiments of the present invention are directed to an x-ray tube that can be implemented within a relatively compact geometry that facilitates, among other things, optimal positioning and placement of the x-ray tube so as to improve the quality of analyses performed with the device, while at the same time substantially minimizing window heating and the formation of filament deposits on the window. Embodiments of the present invention are especially well suited for use in the context of analytical x-ray tubes such as may be utilized in performing close coupled sample analyses. However, it will be appreciated that the features and advantages of the present invention may find useful application in other types of x-ray devices as well.

In a preferred embodiment, the x-ray tube includes a housing that at least partially defines an evacuated enclosure having an x-ray transmissive window at a "nose portion" of the x-ray tube housing. Another portion of the housing defines a cooling chamber portion. That portion of the housing includes a coolant inlet and outlet connection to allow circulation of a coolant medium within the cooling chamber for cooling various components disposed therein. An anode, comprising a body portion and a target surface, and a cathode assembly including an electron source such as a filament, are positioned within the evacuated enclosure so that the anode is between the window and the electron source. A current source and a bias voltage supply are connected to the filament. Optionally, a control grid connected to a voltage supply is disposed substantially proximate to the filament to provide a level of control to the flow of electrons emitted by the filament.

As a result of the placement of the filament some distance away from the window area, filament deposits on the window are substantially prevented. Furthermore, because the filament is removed from the vicinity of the window and target surface, the target surface can be located relatively closer to the window. Such an arrangement facilitates, among other things, a material improvement in the quality of close coupled sample analyses, and a more compact x-ray device geometry—especially in the nose portion of the housing.

Disposed at one end of the anode body is a target surface, preferably comprising tungsten, rhodium or another material chosen to suit the analysis, oriented toward the window. At an opposite end of the anode body, proximate to the cathode assembly, an insulator is disposed that defines a hollow through which electrons traveling from the filament to the anode pass. A drift tunnel is defined through body, which receives the anode allows electrons emitted by the filament and through the insulator to pass through the anode prior to striking the target surface. A high voltage power source connected to the anode maintains a potential difference between the anode and the filament, and between the anode and the evacuated housing. Preferably, the filament and the evacuated housing are at, or near, ground potential. In preferred embodiments, the anode body includes a plurality of extended surfaces so as to facilitate transfer of heat from the anode to a coolant circulating through the cooling chamber portion of the enclosure. Optionally, one or more accelerating and/or positioning coils can be disposed in operative relation to the anode to facilitate control of electron travel parameters, such as speed and direction, of electrons traveling through the drift tunnel.

In operation, electrical power applied to the filament by the power supply causes thermionic emission of electrons from the filament. The current bias voltage supply can be used to control the amount of energy in the electron beam which leave the ground state. This reduction in electron energy helps to slow the electrons somewhat and thus aids in preventing the electrons from impacting the window after they emerge from the drift tunnel.

The high voltage field defined between the anode and the filament causes the emitted electrons to rapidly accelerate through the hollow defined by the insulator. The control grid potential controls the current of the electron beam emitted by the cathode assembly. After passing through the insulator, the accelerated electrons have reached an energy state consistent with the high voltage field and thus substantially cease to accelerate. The electrons pass through the drift tunnel in the anode without gaining any significant additional energy. Optional magnets or positioning coils may be disposed proximate to the anode to facilitate positioning of the electron beam exiting the drift tunnel.

The potential difference between the anode and the window, also at ground potential, causes electrons emerging from the tunnel to rapidly decelerate so that the electrons are substantially prevented from striking the window and nearby structures. Because substantially all of the electrons are prevented from impacting the window, the heating of the window area and adjacent structures is reduced to a level where there is no need for employment of auxiliary window cooling devices.

As a consequence of the deceleration imposed upon the electrons by the high voltage field, substantially all of the electrons exiting from the tunnel slow to a stop and collectively form a cloud of electrons. The electrons in this cloud are subsequently re-accelerated under the influence of the same high voltage field that caused them to decelerate initially, and proceed to rapidly accelerate toward the target surface. Upon impacting the target surface, the accelerating electrons produce x-rays which are then emitted through the window and toward the sample. One or more detectors disposed proximate to the sample sense a characteristic response of the sample and convey corresponding data to a computer for processing and/or analysis.

These and other objects and features of the invention will become more fully apparent from the following description and appended claims, or may be learned by the practice of the invention as set forth hereinafter.

BRIEF DESCRIPTION OF THE DRAWINGS

In order that the manner in which the above recited and other advantages and features of the claimed invention are obtained, a more particular description of the claimed invention briefly described above will be rendered by reference to specific embodiments thereof, which are illustrated in the appended drawings. Understanding that these drawings depict only typical embodiments of the invention as claimed and are not therefore to be considered limiting of its scope, the claimed invention will be described and explained with additional specificity and detail through the use of the accompanying drawings in which:

DETAILED DESCRIPTION OF THE PREFERRED EMBODIMENTS

Reference will now be made to figures wherein like structures will be provided with like reference designations. It is to be understood that the drawings are diagrammatic and schematic representations of various embodiments of the claimed invention, and are not to be construed as limiting the present claimed invention, nor are the drawings necessarily drawn to scale.

Figure 1:
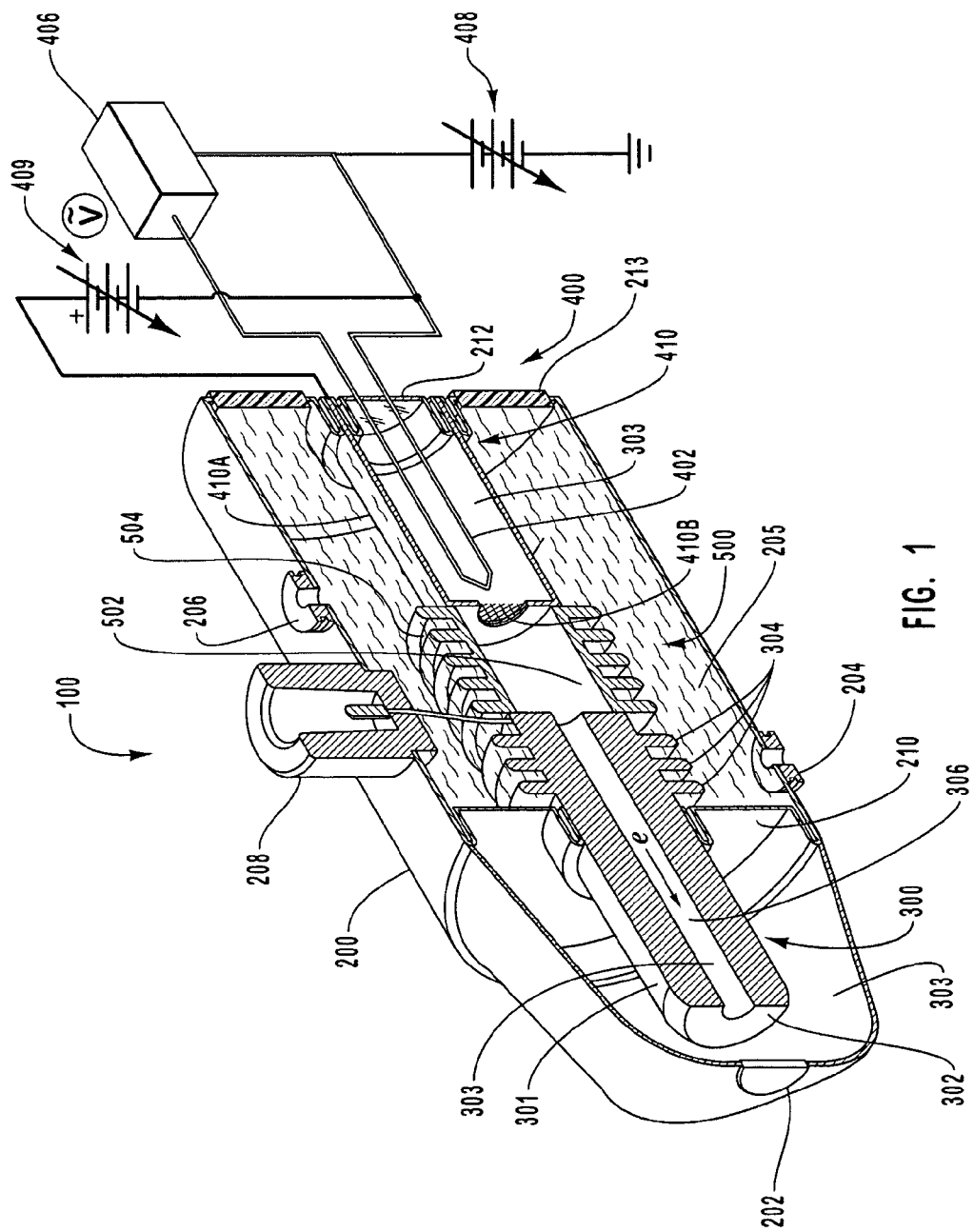
FIG. 1 is a cutaway perspective view indicating various features of an embodiment of an exemplary x-ray tube constructed in accordance with teachings of the present invention.

Directing attention now to FIG. 1, an embodiment of an x-ray tube, such as an analytical x-ray tube ("AXT"), is indicated generally as 100. AXT 100 includes an envelope housing 200 having an x-ray transmissive window 202, preferably comprising beryllium or the like, formed at the "nose portion" end of the housing. Housing 200 further includes a coolant inlet and coolant outlet connection 204 and 206 respectively, so as to permit circulation of a coolant medium throughout an interior coolant chamber portion 205 of the housing, as is discussed in further detail below. Disposed opposite each other within an evacuated portion of the housing 200 is an anode assembly 300 and a cathode assembly 400. The anode 300 is in electrical communication with a high voltage connection 208, which is in turn connected to a suitable high voltage source (not shown). The anode 300 and the cathode assembly 400 are substantially electrically isolated from the housing 200 by insulators 210 and 212, respectively, as well as insulator portion 213. Insulators 210, 212 and 213 comprise a dielectric or other electrically non-conductive material, preferably ceramic, glass, or the like. The insulators also form an air tight seal so as to maintain the relevant interior portions of the housing 200 at a vacuum. In particular, the interior portion indicated at 303 is maintained at a substantial vacuum.

Anode 300 includes a body 301 on which is disposed a target surface 302. Preferably, body 301 of anode 300 substantially comprises a highly conductive metal such as copper or a copper alloy. The target surface 302 is physically arranged and positioned on the body so as to be oriented between the window 202 and the cathode assembly 400.

Preferably, target surface 302 comprises a material having high "Z" number such as tungsten or the like. However it will be appreciated that various other target surface materials may be employed as required to achieve one or more desired results or affects, and depending, in particular, on the type of analysis to be performed. Such materials might include, but are not limited to, molybdenum, chrome, rhodium palladium, silver and alloys thereof.

Figure 2:
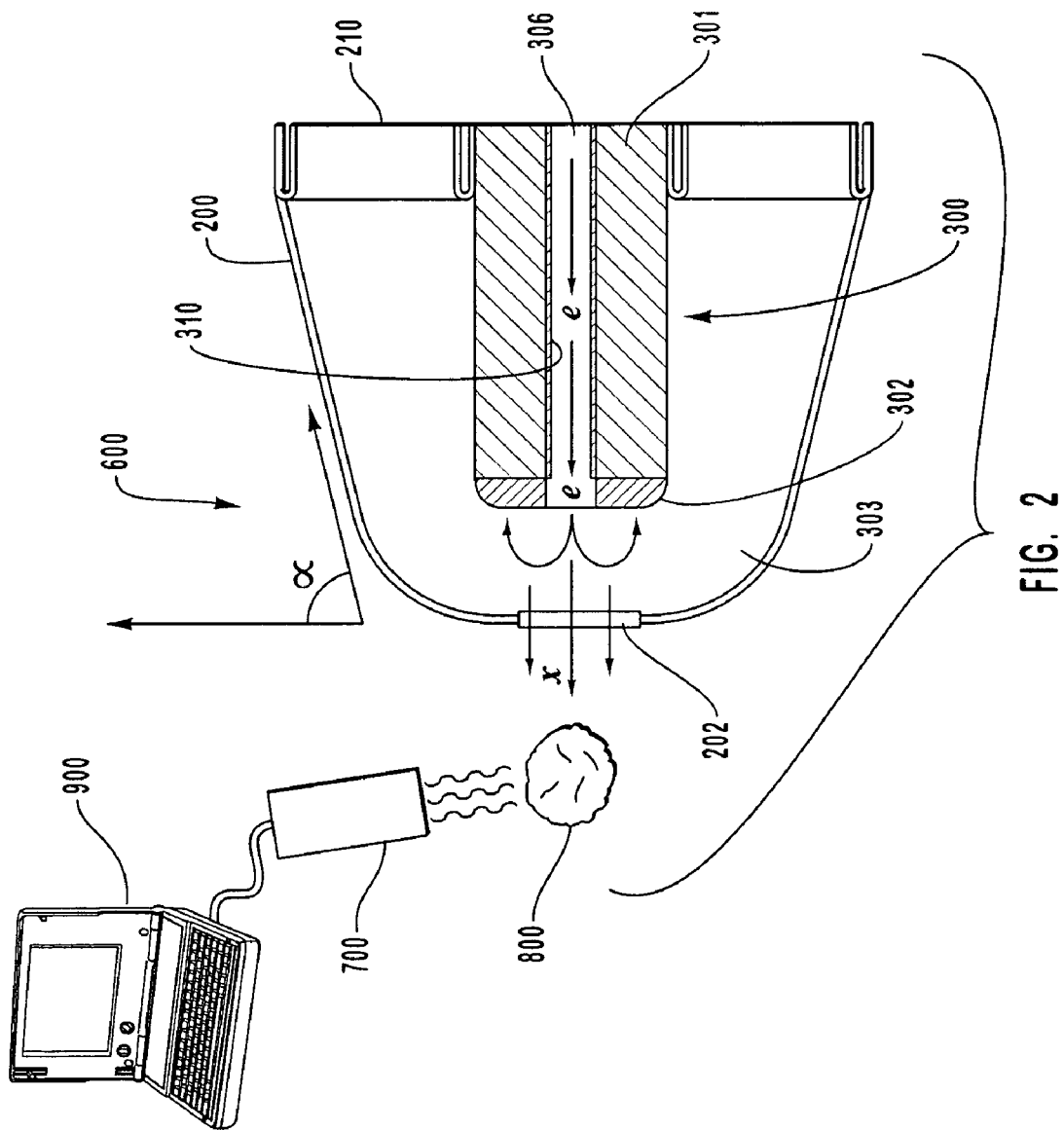
FIG. 2 is a cutaway view of a portion of an embodiment of the tube of FIG. 1 and indicating various details of an embodiment of a system for facilitating close coupled sample analyses.

The anode 300 also includes a drift tunnel 306 formed through the anode body 301 and exiting through the target surface 302. Drift tunnel 306 defines a path that is arranged to receive, at least indirectly, electrons (denoted "e" in FIG. 1) that are emitted by cathode assembly 400. In a preferred embodiment, one or more exterior surfaces of anode 300, and/or an interior portion of drift tunnel 306, are coated with material(s) having substantially the same chemical properties as the target surface 302. One example of this arrangement is shown in FIG. 2 at coating or layer 310. In this way, x-rays emitted from the coated surface(s) will be substantially similar to those that are emitted from the target surface 302.

One embodiment of anode 300 includes a plurality of extended surfaces 304 formed along an outer periphery of the anode body 301. The extended surfaces serve to dissipate heat and facilitate cooling of the anode structure 300. Preferably, the surfaces 304 are positioned within the coolant chamber 205 portion of the housing, so as to be placed in contact with a circulating coolant medium.

It will be appreciated that the arrangement of anode 300 and cathode assembly 400 inside the evacuated portion of the housing 200 permits the target surface 302 of anode 300 to be moved relatively closer to window 202. This is in contrast to typical prior art configurations, which place the cathode in the vicinity of the anode target, thereby increasing the distance between the target and the sample. Positioning the cathode 400 behind the anode 300 also allows the physical geometry of the housing 200 to have a smaller "nose piece" (the forward portion of the housing 200 containing the window 202). This is represented in FIG. 2, which shows how the angle "α" can be increased to provide a narrower, sharper nose piece. This narrower nose piece permits the target surface 302 to be placed relatively closer to the sample (800 in FIG. 2) being analyzed. Again, this increases the precision of the analysis.

With continued attention to FIG. 1, additional details are provided regarding the structure of cathode assembly 400. In particular, cathode assembly 400 includes an electron source 402, such as a filament comprising tungsten or the like. The filament 402 is connected to a filament power supply 406, and in a preferred embodiment a cathode bias voltage supply 408. In one embodiment, the filament power supply 406 comprises an alternating voltage source. It will be appreciated however that filament power supply 406 may alternatively comprise a direct voltage source. Preferably, cathode bias voltage supply 408 is a variable type and comprises a direct current (d.c.) source, such as a battery or the like.

In some embodiments, it may be desirable to provide a control grid 410 between the electron source 402 and the anode 300. The control grid 410 can be used to control the flow of electrons emitted from electron source 402 by applying a grid potential between control grid 410 and electron source 402. In one embodiment, control grid 410 comprises a metal grid tube 410A disposed about electron source 402. The grid tube 410A defines an opening in which is disposed grid mesh 410B through which electrons emitted from electron source 402 pass. The grid potential is supplied via an external voltage source 409.

Interposed between cathode assembly 400 and anode 300 is an insulator 500 which serves, among other things, to substantially electrically isolate anode 300 and cathode assembly 400. Insulator 500 comprises a dielectric or other electrically non-conductive material, preferably ceramic, glass, or the like. Moreover, the insulator 500 defines a hollow 502 portion substantially aligned with drift tunnel 306 of anode 300. The hollow 502 of insulator 500 is maintained at a vacuum and is likewise substantially aligned with electron source 402 of cathode assembly 400 so as to allow passage of the electron beam. It will be appreciated however, that the relative alignments between hollow 502, drift tunnel 306, and/or electron source 402 may be varied as required to achieve one or more desired results or effects. One embodiment of insulator 500 includes a plurality of extended surfaces 504 which serve to facilitate cooling of insulator 500 and other AXT 100 structures. Like extended surfaces 304, the insulator extended surfaces 504 are positioned within the coolant chamber 205 portion of the housing.

With continuing reference to FIG. 1, various features pertaining to the operation of AXT 100 are discussed in further detail. In operation, electrical current applied to filament 402 by filament supply 406 causes electrons, denoted "e," to be emitted by the process of thermionic emission. Because filament supply 406 applies various potentials to the filament, the energy level of electrons "e" emitted from electron source 402 varies accordingly. Electrons with excessively high energy levels may overcome the decelerating effect, discussed in further detail below, imposed by the high voltage field between anode 300 and housing 200, and thereby impact window 202. Accordingly, the energy level of the electrons can be adjusted so as to preclude this result. As discussed below, cathode bias voltage supply 408 serves to afford a measure of control over the energy level of the electrons emitted from electron source 402.

In particular, cathode bias voltage supply 408 is preferably adjusted so as to impose a slightly positive (+) bias on electron source 402. This slightly positive bias serves at least two purposes. First, the bias dampens effects imposed upon the electrons by filament supply 406 by reducing the energy level at which the electrons leave the ground state. Additionally, the reduction in electron energy facilitates adjustment of various aspects and parameters of the electron beam emitted by filament 402, including, but not limited to, the focus of the electron beam on target surface 302.

Further control over the electrons and electron beam can also be provided by the control grid 410. In particular, control grid 410 may be employed to control, at least, the energy level of electrons emitted by electron source 402 which impact target surface 302 of anode 300. This is achieved by varying the potential difference, or "grid potential," between control grid 410 and electron source 402. In a preferred embodiment, a voltage source 409 in communication with control grid 410 establishes a grid potential which provides an electrical field that nullifies to a desired extent, or alternatively, reinforces, the potential between electron source 402 and anode 300. More specifically, the strength of the electrical field resulting from the grid potential can desirably be adjusted to repel the electrons to a varying extent and control the energy level.

In view of the foregoing, it will be appreciated that the grid potential can be varied to a virtually unlimited extent so as to facilitate achievement of one or more desired results or effects with regard to the emission of electrons from electron source 402 and, accordingly, the rate of x-ray production. In addition to controlling electron flow, control grid 410 can also be employed to completely prevent or stop electron flow. Specifically, the grid potential can be adjusted so that the potential between electron source 402 and anode 300 is completely nullified, and thus the flow of electrons from electron source 402 to anode 300 is prevented altogether. Notwithstanding the foregoing, it will be appreciated that control grid 410 may be neither required or desired in some applications.

Control grid 410 may also be employed to facilitate a desirable increase in the "perveance" of AXT 100 in low power applications. As is well known, the perveance of a particular electron source is related to the number of electrons discharged by the electron source and received at a target surface disposed a given distance away from the electron source. In general, a given target surface receives relatively more electrons from an electron source having a relatively higher perveance than from an electron source with a relatively lower perveance. Thus, the perveance value of a given electron source is proportional to the number of electrons discharged by that electron source and received at the target surface.

By providing control over electron flow, control grid 410 is thus able to ensure that relatively more electrons reach target surface 302 than would be the case where uncontrolled emission of electrons occurs. In this way, control grid 410 serves to facilitate a desirable increase in the perveance of AXT 100. It will be appreciated that this is a particularly useful feature in those cases where the power of the x-ray device, expressed as the potential between the target surface and electron source, is relatively low.

With continuing attention now to details of the operation of AXT 100, the high voltage field between anode 300 and electron source 402 causes electrons emitted from electron source 402 to rapidly accelerate through hollow 502 of insulator 500 and pass into drift tunnel 306 of anode 300. As previously noted, this high voltage field is preferably created by connecting a high voltage source at high voltage connection 208 of evacuated housing 200, while simultaneously maintaining electron source 402 at, or near, ground potential.

Figure 3:
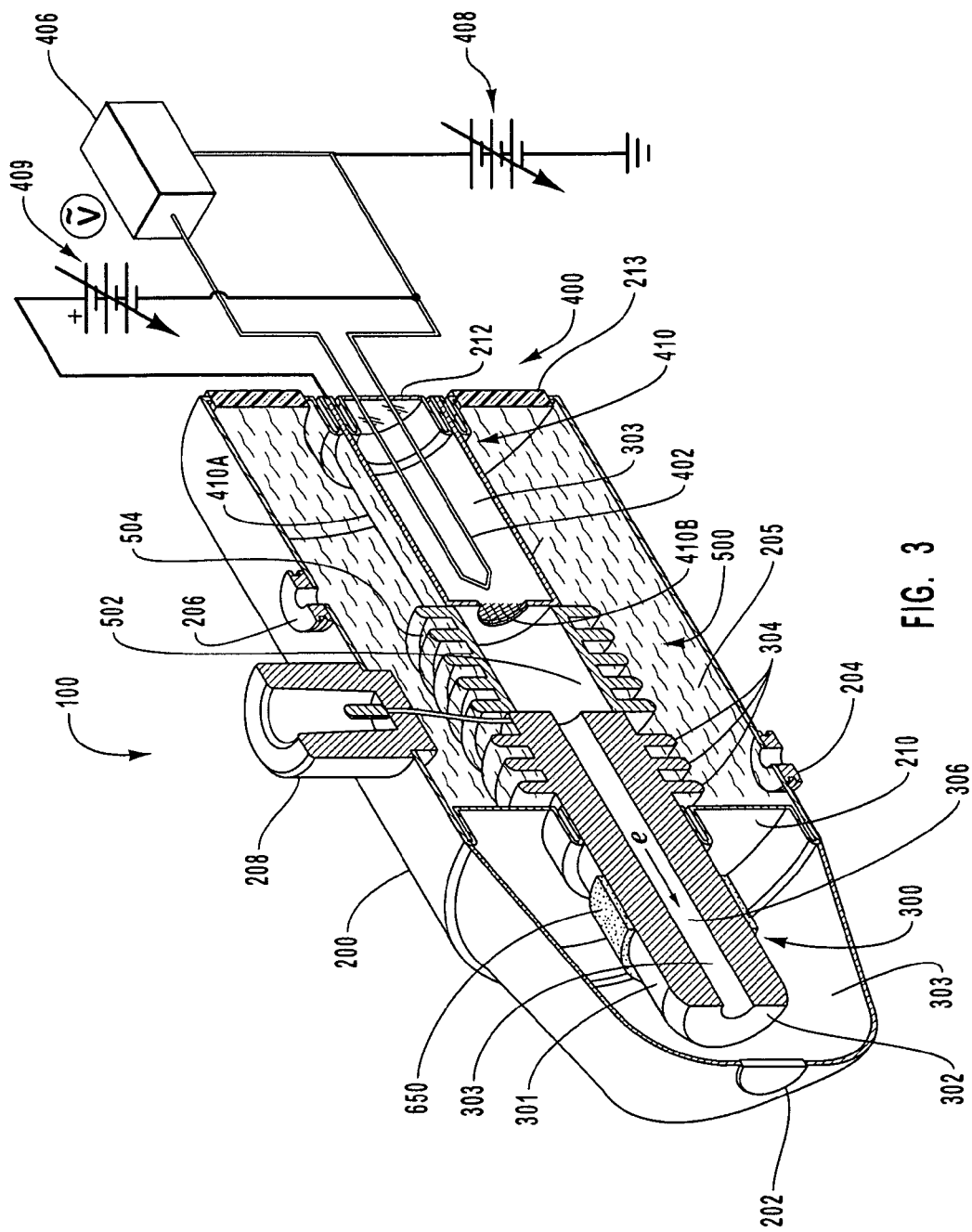
FIG. 3 is a cutaway perspective view illustrating another embodiment of an x-ray tube.

It will be appreciated that the beam of electrons thus produced can be controlled or adjusted in a variety of ways so as to facilitate achievement of one or more desired effects or results. For example, embodiments of the present invention which typically experience high perveance variations may employ an axial confining magnetic field so as to confine, steer and/or otherwise control and manipulate the beam of electrons emitted by electron source 402 inside drift tunnel 306. Establishment of such axial confining magnetic fields can be achieved with a variety of structures and devices including, but not limited to, permanent magnets, solenoids, coils or the like. FIG. 3 illustrates one such alternative embodiment, wherein a permanent magnet 650 (or coil, etc.) is positioned about a periphery of the anode structure 300.

In one embodiment, the electrons emitted by electron source 402 simply drift through drift tunnel 306 after having been accelerated by the high voltage field between anode 300 and electron source 402. That is, by the time the electrons emitted from electron source 402 have entered drift tunnel 306, they have achieved an energy level consistent with the potential difference between electron source 402 and anode 300. Thus, no additional acceleration of the electrons occurs as they pass through drift tunnel 306, and the electrons accordingly do not gain additional energy while in drift tunnel 306.

In an alternative embodiment, AXT 100 includes one or more accelerating and/or positioning coils disposed proximate to anode 300 so as to control such travel parameters as the speed and direction of electrons passing through drift tunnel 306. It will be appreciated that such accelerating and/or positioning coils may be employed to perform a variety of functions including, but not limited to, accelerating the electrons as they pass through drift tunnel 306. As another example, accelerating and/or positioning coils may be employed to establish a magnetic or electrostatic field which can be used to control the position and orientation of the electron beam, such as is represented in the alternative embodiment of FIG. 3.

FIG. 2 provides additional details regarding the production of x-rays by AXT 100. In particular, as the electrons "e" exit drift tunnel 306 and travel toward window 202 of housing 200, the potential difference between housing 200 and window 202, both of which are at substantially ground potential, and the anode 300, causes substantially all of the electrons to decelerate rapidly and ultimately stop before they can impact window 202. It will be appreciated that reducing the number of electrons greatly reduces the heat levels typically experienced in window 202 and adjacent structures. This reduces the need for auxiliary cooling systems and devices in the window area.

The electrons thus decelerated and stopped collectively form an electron cloud disposed between window 202 and target surface 302. As suggested in FIG. 2, the positive potential difference between window 202 and target surface 302 of 300 then causes electrons in the cloud to re-accelerate rapidly towards target surface 302 of anode 300. It will be appreciated that by controlling the rate at which electrons "e" exit drift tunnel 306 permits variations in the spacing between window 202 and target surface 302.

As is well known, a potential such as that which exists between housing 200 and target surface 302 has characteristic electrical field lines. By definition, electrical field lines indicate the direction an electron will travel when placed in that field. Thus, the electrons accelerating toward target surface 302 tend to travel along the electrical field lines defined by the potential. Because a majority of the electrical field lines terminate on target surface 302, and not inside drift tunnel 306, there is little likelihood that accelerating electrons will re-enter drift tunnel 306.

It will be appreciated that at least window 202 and target surface 302 may desirably be shaped, arranged, and/or sized as desired so as to facilitate achievement of one or more desired effects with respect to parameters such as the arrangement and strength of the potential between window 202 and target surface 302, and the direction and orientation of the electrical field lines. Additional examples of features that may be adjusted include, but are not limited to, the length and shape of drift tunnel 306, the relative alignment of drift tunnel 306 with hollow 502, and the orientation of window 202 with respect to target surface 302. Furthermore, as previously noted, the geometry of the target surface and/or the drift tunnel 306 proximate to target surface 302 may be defined so as to cause electrons exiting drift tunnel 306 to follow a particular desired path to target surface 302.

Control of the electrons traveling toward target surface 302 may be achieved in other ways as well. For example, as noted in connection with FIG. 3, various devices such as positioning coils and the like may be employed to generate electrostatic positioning and magnetic field forces that can be used to guide the electrons to target surface 302.

Upon striking target surface 302 of anode 300, some of the kinetic energy of the electrons generates x-rays which are emitted through window 202. The coating 310 (FIG. 2) inside drift tunnel 306, preferably comprising substantially the same material (or at least having similar x-ray generating characteristics) as target surface 302, helps ensure that any x-rays produced as a result of interaction between electrons and the interior of drift tunnel 306 are of a nature consistent with those emitted from target surface 302. The coating thus helps avoid contamination of x-rays emitted by AXT 100 and, accordingly contributes to improved quality of sample analyses. Additionally, it will be appreciated that exterior surfaces of body 301 of anode 300 may likewise be coated so as to preclude contamination of x-rays emitted by AXT 100 when stray electrons strike those surfaces.

With specific reference now to FIG. 1, embodiments of the present invention include provisions for cooling which serve to adequately remove sufficient heat as to facilitate reliable operation of AXT 100 without adding unnecessary bulk. In particular, it was noted earlier that anode 300 and insulator 500 include extended surfaces 304 and 504, respectively. Furthermore, other extended surfaces or cooling structures disposed either inside or outside housing 200 may be likewise be employed to facilitate or augment cooling of AXT 100.

In operation, a flow of coolant entering the housing 200 by way of coolant inlet connection 204 flows over extended surfaces 304 and 504 so that at least some heat from anode 300 and insulator 500 is transferred to the coolant. Air tight seals between control grid 410 and insulator 500, and between insulator 500 and anode 300, prevent coolant from entering the interior of those structures. After absorbing heat from AXT 100, the coolant then exits the interior portion 205 of the housing 200 by way of coolant outlet connection 206. Upon exiting the housing 200, at least some heat is removed from the coolant by way of an external cooling unit (not shown) and then returned to the housing 200 to repeat the cycle. Embodiments of the present invention may include various types of instrumentation such as pressure gauges, flow meters, and the like to monitor coolant flow parameters such as pressure and temperature.

The coolant used preferably comprises a dielectric oil such as Shell Diala AX. Alternatively, a flow of forced air or suitable dielectric gas may be used as a coolant in some applications. However, any coolant that would be suitable for use in the operating environment of AXT 100 is contemplated as being within the scope of the present invention. Such coolants include, but are not limited to, substantially dielectric liquid coolants as well as dual phase dielectric liquid-vapor, coolants.

FIG. 2 depicts an embodiment of a close-coupled analysis system, indicated generally at 600. In particular, one embodiment of a close-coupled sample analysis system 600 includes an AXT 100 and one or more detectors 700. Preferably, AXT 100 and detectors 700 are placed as close as possible to sample 800 so as to facilitate effectuation of high quality sample analyses.

In operation, x-rays emitted from AXT 100, denoted as "x" in FIG. 2, pass through window 202 of AXT 100 and impinge upon sample 700. As a result of receiving energy from AXT 100, in the form of x-rays, sample 800 manifests a characteristic response which is sensed by detector 700. It will be appreciated that the characteristic response of sample 800 will vary in accordance with the values of parameters including, but not limited to, the structure and chemical composition of sample 800. In some applications for example, sample 800 will fluoresce when impacted by x-rays emitted from AXT 100. With reference to the foregoing example, the fluorescence of sample 800 is then sensed by detector 700. In this example, detector 700 would be of a type suitable for sensing fluorescence of sample 800. However, it will be appreciated that various other types of detectors 700 may be employed depending upon the characteristic response likely to be manifested by a particular sample 800 in response to the impingement of x-rays. Furthermore, the number and positioning of detectors 700 may be varied as required to suit a particular analytical situation or scenario.

By evaluating the characteristic response(s) sensed by detector 700, the user of AXT 100 can, at least indirectly, draw certain conclusions regarding such variables as the chemical composition and structure of sample 800. Accordingly, one embodiment of close-coupled sample analysis system 700 further includes a computer 900 to which data sensed and accumulated by detectors 800 can be downloaded for processing and analysis. Analyses performed by embodiments of the present invention include, but are not limited to, spectral analyses and the like.

It will be appreciated from the foregoing discussion that embodiments of the present invention possess a variety of useful features. Some of these features are summarized briefly as follows. For example, the fact that target surface 302 is interposed between electron source 402 and window 202 substantially prevents tungsten emissions from electron source 402 from coating window 202. Thus, regardless of the heat applied to electron source 402, window 202 can remain substantially free from coating by way of electron source 402 emissions.

Furthermore, by decelerating the electrons exiting drift tunnel 306 and otherwise preventing them from striking the window reduces the heat levels typically experienced in the area of window 202. Such heat reductions obviate the need for bulky and expensive auxiliary cooling devices and systems. This reduction in heat levels also contributes to improvements in the service life and performance of window 202, and of AXT 100 as a whole.

Additionally, because electron source 402 is not required to be interposed between window 202 and target surface 302, as is the case in many known devices, target surface 302 can be moved relatively closer to window 202 and, therefore, relatively closer to sample 800. Such arrangements permit a relative increase in the number of electrons that strike target surface 302 and consequently, a relative increase in the number of x-rays produced. As a result of the increased number of electrons striking sample 800, improved analyses of samples are thereby facilitated.

Finally, it will be appreciated that by removing electron source 402 from the general vicinity of window 202, that portion of AXT 100 in which window 202 can be made relatively more compact so as to facilitate achievement of a more compact nose angle, and thereby permit the placement of target surface 302 relatively close to the sample(s) to be analyzed.

The present claimed invention may be embodied in other specific forms without departing from its spirit or essential characteristics. The described embodiments are to be considered in all respects only as illustrative, and not restrictive. The scope of the claimed invention is, therefore, indicated by the appended claims rather than by the foregoing description. All changes that come within the meaning and range of equivalency of the claims are to be embraced within their scope.

What is claimed and desired to be secured by United States Letters Patent is:

1. An x-ray device comprising:
    (a) an enclosure including an x-ray transmissive window;
    (b) a cathode assembly disposed within the enclosure, the cathode assembly including an electron source capable of emitting electrons;
    (c) an anode including a body portion and a target surface, the target surface being positioned on the body portion so as to face away from the electron source of the cathode assembly, the anode being disposed within the enclosure so as to be positioned between the cathode assembly and the window, the anode further including a drift tunnel that defines a path through which electrons pass from the electron source to the target surface; and (d) at least one voltage source electrically connected so as to provide at least one potential field that causes at least some of the electrons to impact the target surface and produce x-rays for emission through the window.

2. The x-ray device of claim 1, further comprising at least one acceleration coil disposed proximate to said anode, said at least one accelerating coil facilitating acceleration of electrons in said drift tunnel.

3. The x-ray device of claim 1, further comprising at least one positioning coil, said at least one positioning coil controlling at least one travel parameter of at least some electrons in said drift tunnel.

4. The x-ray device of claim 1, wherein at least a portion of the enclosure forms a cooling chamber that receives a coolant medium.

5. The x-ray device of claim 1, wherein the at least one voltage source includes a grid power source electrically connected to a control grid so that a predetermined grid potential can be selectively provided in a path of the electrons emitted from the electron source to the anode.

6. The x-ray device of claim 5, wherein the grid potential is variable.

7. The x-ray device of claim 5, wherein the grid potential is negative.

8. The x-ray device of claim 1, further comprising an insulator disposed between the anode assembly and the cathode assembly, said insulator serving to substantially electrically isolate the anode assembly and the cathode assembly from each other.

9. The x-ray device of claim 8, wherein the insulator defines a path through which electrons emitted by said electron source pass prior to entering the drift tunnel.

10. The x-ray device of claim 1, wherein the at least one voltage source includes a cathode bias voltage supply in electrical communication with said electron source, said cathode bias voltage capable of placing the electron source at a predetermined voltage potential.

11. The x-ray device of claim 1, further comprising a layer of material disposed at least partially on one surface of the drift tunnel, the layer of material being comprised of a material having x-ray generation characteristics substantially similar to a material comprising the target surface.

12. The x-ray device of claim 1, wherein the electron source comprises a filament, the filament in electrical communication with a filament supply so as to facilitate thermionic emission of electrons from said filament.

13. The x-ray device of claim 1, wherein the at least one voltage source is capable of providing a voltage potential that prevents substantially all electrons exiting the drift tunnel from impacting the window.

14. An x-ray tube useful in performing close coupled sample analyses, the x-ray tube including a housing having an x-ray transmissive window, the housing defining an evacuated interior portion and a cooling chamber portion configured to receive a flow of coolant, the x-ray tube comprising:

(a) a cathode structure including a filament capable of emitting electrons, the filament being disposed within the evacuated portion of the housing; and (b) an anode structure having a body portion upon which a target surface is disposed, the body portion defining a portion of a drift tunnel whose interior surface is at least partly coated with a material having substantially the same chemical characteristics as a material of which the target surface is comprised, the anode structure including a target surface disposed within the evacuated portion of the housing so as to be positioned between the window and the cathode structure, the target surface being further positioned so as to be impacted by at least some electrons emitted by the filament to produce x-rays that can be released through the window.

15. The x-ray tube of claim 14, wherein the anode structure further comprises at least one extended surface in substantial contact with a coolant contained within the cooling chamber.

16. The x-ray tube of claim 14, wherein the anode structure is comprised of a material selected from the group consisting of copper, and copper alloys.

17. The x-ray tube of claim 14, wherein the target surface is positioned substantially proximate to the window.

18. The x-ray tube of claim 14, wherein the target surface comprises a material selected from the group consisting of tungsten, and tungsten alloys.

19. A method for generating x-rays for emission from an x-ray tube, the method comprising the steps of:

(a) emitting a flow of electrons within an evacuated enclosure;

(b) applying a first field potential to accelerate the electrons in the direction of an x-ray tube transmissive window disposed on the evacuated enclosure;

(c) decelerating the electrons as they approach the window so as to substantially prevent the electrons from striking the window;

(d) re-accelerating at least some of said decelerated electrons towards a target surface disposed within the evacuated enclosure so that at least some of said re-accelerated electrons impact the target surface and produce x-rays; and (e) emitting the x-rays through the window.

20. The method of claim 19, further comprising the step of adjusting an energy level of at least some of the emitted electrons.

21. The method of claim 20, wherein the step of adjusting an energy level comprises the step of imposing a negative bias on the emitted electrons.

22. The method of claim 19, further comprising the step of controlling at least one travel parameter of at least some electrons traveling towards the window.

23. The method of claim 19, further comprising the act of controlling said flow of electrons traveling towards the window with a negative grid potential.

24. A method for generating x-rays for emission from an x-ray tube, the method comprising the steps of:

(a) emitting electrons from a filament disposed within an evacuated enclosure;

(b) accelerating the electrons through an insulator in a high voltage field;

(c) allowing the electrons to drift through a drift tunnel formed through an anode;

(d) decelerating the electrons in a reverse high voltage field as the electrons approach a window disposed on the evacuated enclosure;

(e) re-accelerating the decelerated electrons in a high voltage field towards a target surface to produce x-rays; and (f) directing the x-rays through the window.

25. The method as defined in claim 24, further comprising the step of biasing the filament to control the energy of the emitted electrons.

26. A system for performing close coupled sample analyses, the system comprising:

(a) an x-ray tube, the x-ray tube including:

(i) an enclosure housing an evacuated portion including a window;

(ii) an electron source disposed within said evacuated enclosure;

(iii) an anode having a body portion upon which a target surface is disposed, and said anode being disposed within said evacuated enclosure so that said body portion and said target surface are interposed between said electron source and said window, and said body portion and said target surface collectively defining a portion of a drift tunnel that extends through said body portion and said target surface and is positioned so that electrons emitted by said electron source pass through said drift tunnel and impact said target surface so as to produce x-rays for emission through said window; and (b) at least one detector, said at least one detector being disposed proximate to the sample so that when x-rays emitted by said x-ray tube impact the sample said at least one detector senses a characteristic response of the sample.

27. The system of claim 24, wherein said characteristic response comprises fluorescence.

28. The system of claim 24, further comprising at least one computer in at least indirect communication with said at least one detector, said at least one computer facilitating evaluation of said characteristic response.

29. The system of claim 26, wherein said evaluation comprises spectral analysis.

* * * * *

UNITED STATES PATENT AND TRADEMARK OFFICE
CERTIFICATE OF CORRECTION

PATENT NO. : 7,593,509 B2  Page 1 of 1
APPLICATION NO. : 11/863124
DATED : September 22, 2009
INVENTOR(S) : Richardson et al.

It is certified that error appears in the above-identified patent and that said Letters Patent is hereby corrected as shown below:

Column 5
Line 3, change "through body" to --through anode body--
Line 4, delete "receives the anode"
Line 24, change "leave" to --leaves--

Column 11
Line 50, change "700" to --800--

Column 12
Line 7, change "800" to --700--

Signed and Sealed this

Sixth Day of July, 2010

David J. Kappos
*Director of the United States Patent and Trademark Office*